(12) United States Patent
Wong et al.

(10) Patent No.: US 8,975,419 B2
(45) Date of Patent: Mar. 10, 2015

(54) LOW BANDGAP DICYANOVINYL AND TRICYANOVINYL OLIGOTHIOPHENES FOR SOLAR CELL APPLICATIONS

(71) Applicant: Nano and Advanced Materials Institute Limited, Hkust, Clear Water Bay (HK)

(72) Inventors: Ricky Man-Shing Wong, Clear Water Bay (HK); Weifeng Zhang, Clear Water Bay (HK); Lei Guo, Clear Water Bay (HK)

(73) Assignee: Nano and Advanced Materials Institute Limited, Hong Kong (HK)

( * ) Notice: Subject to any disclaimer, the term of this patent is extended or adjusted under 35 U.S.C. 154(b) by 0 days.

(21) Appl. No.: 13/930,681

(22) Filed: Jun. 28, 2013

(65) Prior Publication Data

US 2014/0005411 A1  Jan. 2, 2014

Related U.S. Application Data

(60) Provisional application No. 61/690,572, filed on Jun. 29, 2012.

(51) Int. Cl.
*C07D 327/04* (2006.01)
*C07D 327/10* (2006.01)
*H01L 51/00* (2006.01)
*H01L 51/42* (2006.01)

(52) U.S. Cl.
CPC .......... *H01L 51/006* (2013.01); *H01L 51/0061* (2013.01); *H01L 51/0072* (2013.01); *H01L 51/0068* (2013.01); *H01L 51/0064* (2013.01); Y02E 10/549 (2013.01); H01L 51/4253 (2013.01)
USPC .............................. 549/30; 549/31

(58) Field of Classification Search
None
See application file for complete search history.

(56) References Cited

U.S. PATENT DOCUMENTS 7,569,704 B1 * 8/2009 Lin et al. .................. 548/442
2014/0005411 A1   1/2014 Wong et al.

FOREIGN PATENT DOCUMENTS

JP      2009266633 A  * 11/2009
WO   WO 2010/147427 A2   12/2010
WO   WO 2013/061958 A1   5/2013

OTHER PUBLICATIONS

Chen, Yung-Chung et al. Chemistry-A European Journal 18(17) (2012) 5430-5437.*
Yen, et al., The Journal of Physical Chemistry, C, (2008), 112(32), pp. 12557-12567.*
Xia, et al., Adv. Mater. (2008), 20, 4810-4815.*
Huang, et al., Journal of Physical Chemistry C (2008), 112(49), 19739-19747.*
Xia, et al., The Journal of Physical Chemistry, C, (2008), 112(42), pp. 16714-16720.*
Hao Qin, et al., An Organic Sensitizer with a Fused Dithienothiophene Unit for Efficient and Stable Dye-Sensitized Solar Cells, Journal American Chemical Society, Jun. 27, 2008, 9202-9203, vol. 130, No. 29.
Ji Zhang, et al., Density functional theory characterization and design of high-performance diarylamine-fluorene dyes with different spacers for dye-sensitized solar cells, Journals of Materials Chemistry, 2012, 568-576, 22.
Ping Fang, et al. Donor-Acceptor Oligothiophenes as Low Optical Gap Chromophores for Photovoltaic Applications, Advanced Materials, 2008, 4810-4815, 20.
Jooyoung Kim, et al., Efficient small molecule organic semiconductor containing bisdimethylfluorenyl amino benzo [b]thiophene for high open circuit voltage in high efficiency solution processed organic solar cell, RSC Advances, 2012, 2692-2695, 2.
Haye Min Ko, et al., Molecular engineering of push-pull chromophore for efficient bulk-heterojunction morphology in solution processed small molecule organic photovoltaics, Journal of Materials Chermistry, 2011, 7248-7253, 21.
Weifeng Zhang, et al., Solution processable donor-acceptor oligothiophenes for bulk-heterojunction solar cells, Journal of Materials Chemistry, 2010, 2182-2189, 20.
Ping Fang Xia, et al., Triarylamino and Tricyanovinyl End-Capped Oligothiophenes with Reduced Optical Gap for Photovoltaic Applications, Journal Physical Chemistry, 2008, 16714-16720, vol. 112, No. 42.

* cited by examiner

Primary Examiner — Nyeemah A Grazier
(74) Attorney, Agent, or Firm — Renner Kenner Greive Bobak Taylor & Weber (57) ABSTRACT

The invention relates to solution-processable, p-type, low-optical gap oligothiophene compounds for use in solar cell application, comprising at least one thiophene-containing group, at least one electron-withdrawing dicyanovinyl or tricyanovinyl group, and at least one electron-donating diphenylaminofluorenyl or N-alkylcarbazole group.

4 Claims, 1 Drawing Sheet

LOW BANDGAP DICYANOVINYL AND TRICYANOVINYL OLIGOTHIOPHENES FOR SOLAR CELL APPLICATIONS

FIELD OF THE INVENTION

The invention relates to a synthetic compound for solar cell applications. Particularly but not exclusively, the invention also relates to an oligothiophene compound for solar cell applications.

BACKGROUND OF THE INVENTION

Fossil fuels are still one of the major energy sources nowadays. Example of fossil fuels such as coal, petroleum and natural gas are non-renewable natural resources which take thousands of years to form, and are costly to harvest. In addition, combustion of the fossil fuels generates large amount of carbon dioxide as well as undesirable air pollutants. To resolve this, clean and renewable energy resources such as solar energy which can be directly captured and converted to electrical energy by solar cells have been extensively researched and investigated. For example, photovoltaic (PV) technologies have been employed to fabricate different types of solar cells, such as crystalline silicon solar cells, amorphous silicon solar cells, dye-sensitized solar cells, copper indium gallium selenide (CIGS) solar cells and organic solar cells, etc.

Among the solar cells manufactured by various PV technologies, organic solar cells are known to have the advantages of low-cost and high process flexibility in production. Particularly, organic solar cells such as bulk heterojunction (BHJ) photovoltaic (PV) devices have been receiving considerable attention from both the academia and the industry as being promising alternative renewable energy sources due to their relatively low-cost, light-weight, ease of large-area fabrication by solution-process and compatibility to flexible substrate.

SUMMARY OF THE INVENTION

In accordance with an aspect of the present invention, there is provided a compound for use in solar cell application comprising:
- at least one thiophene-containing group;
- at least one electron-withdrawing group comprises at least one cyanovinyl group; and
- at least one electron-donating group;

wherein the at least one electron-donating group is selected from a group consisting of diphenylaminofluorenyl group, N-alkylcarbazole group, and a mixture thereof.

In an embodiment of this aspect, the at least one cyanovinyl group is selected from a group consisting of dicyanovinyl group, tricyanovinyl group, and a mixture thereof.

In an embodiment of this aspect, the compound having a structure of Formula I:

In an embodiment of this aspect, the compound having a structure of Formula II:

(Formula II)

In an embodiment of this aspect, the compound having a structure of Formula III:

(Formula III)

wherein n is selected from a range of 1 to 2.

(Formula I)

wherein n is selected from a range of 2 to 3.

In an embodiment of this aspect, the compound having a structure of Formula IV:

(Formula IV)

wherein n is selected from a range of 1 to 2.

In an embodiment of this aspect, the compound having a structure of Formula V:

(Formula V)

DETAILED DESCRIPTION OF THE PREFERRED EMBODIMENTS

Without wishing to be bound by theory, the inventor through trials, research, study and review of results and observations is of the opinion that the application of oligothiophene compound for BHJ solar cells has beneficial effects. Through the improvement of the material properties, fabrication techniques and device structures, the power conversion efficiencies (PCE) of the BHJ PV cells based on solution-processable p-type conjugated semiconducting materials blended with a soluble fullerene derivative such as [6,6]-phenyl C61-butyric acid methyl ester (PCBM) have recently reached higher than 8-9% (Z. He, C. Zhong, S. Su, M. Xu, H. Wu, Y. Cao, *Nat. Photon.* 2012, 6, 591; X. Li, W. C. H. Choy, L. Huo, F. Xie, W. E. I. Sha, B. Ding, X. Guo, Y. Li, J. Hou, J. You, Y. Yang, *Adv. Mater.* 2012, 24, 3046; J. You, L. Dou, K. Yoshimura, T. Kato, K. Ohya, T. Moriarty, K. Emery, C.-C. Chen, J. Gao, G. Li, Y. Yang, *Nat. Commun.* 2013, 4, 1446; L. Dou, J. You, J. Yang, C.-C. Chen, Y. He, S. Murase, T. Moriarty, K. Emery, G. Li, Y. Yang, *Nat. Photon.* 2012, 6, 180; T.-Y. Chu, J. Lu, S. Beaupre, Y. Zhang, J.-R. Pouliot, J. Zhou, A. Najari, M. Leclerc, Y. Tao, *Adv. Funct. Mater.* 2012, 22, 2345). In addition to polymers, i-conjugated small molecules have been found attractive as alternative solution-processable p-type donor materials because of monodispersity, ease of obtaining in high purity and reproducible properties. As a result, the use of solution-processable small molecules for PV applications has also drawn considerable attention. Meanwhile, solution-processable small molecule-based organic thin-film solar cells have also advanced significantly with efficiencies more than 7% recently (J. Zhou, X. Wan, Y. Liu, Y. Zuo, Z. Li, G. He, G. Long, W. Ni, C. Li, X.-C. Su, Y. Chen, *J. Am. Chem. Soc.* 2012, 134, 16345; Y. Sun, G. C. Welch, W. L. Leong, C. J. Takacs, G. C. Bazan, A. J. Heeger, *Nat. Mater.* 2011, 11, 44; A. Mishra, P. Bäuerle, *Angew. Chem. Int. Ed.* 2012, 51, 2020; R. Fitzner, E. Mena-Osteritz, A. Mishra, G. Schulz, E. Reinold, M. Weil, C. Korner, H. Ziehlke, C. Elschner, K. Leo, M. Riede, M. Pfeiffer, C. Uhrich, P. Bäuerle, *J. Am. Chem. Soc.* 2012, 134, 11064; T. S. van der Poll, J. A. Love, T.-Q. Nguyen, G. C. Bazan, *Adv. Mater.* 2012, 24, 3646). However, more efficient and stable devices would still need further development of superior materials as well as processing and device optimization before commercialization can be realized. Among the factors that limit the PCE of the heterojunction PV cells, the poor sunlight harvesting efficiency and the low charge carrier transport efficiency of organic semiconducting materials are the most determining ones. Thus, the developments of new p-type organic/polymer semiconductors that possess a broad absorption and narrow band gap with high charge carrier mobility are prerequisite for achieving high efficiency organic PV cells.

The use of the intramolecular charge-transfer from an electron-rich unit to an electron-deficient unit has become a promising approach to obtain low bandgap molecular/polymer systems. In addition, the choice of the electron-rich and/or electron-deficient moieties provide a means to proper control of the positions of the frontier molecular orbitals of the donor and acceptor materials which are indispensable to achieve effective excitation dissociation at the heterojunction and a large open-circuit voltage ($V_{oc}$) of a solar cell and also directly related to the photo-oxidation stability of the semiconducting materials.

The inventors' previous studies of the bilayer heterojunction PV cells based on these tricyanovinyl-based chromophores as a donor material and $C_{60}$ as an acceptor material showed a PCE up to 1.33% with a large open-circuit voltage of 0.82 V in the annealed devices.

In another effort, the solution-processed bulk heterojunction PV cells fabricated from penta- and hexa-thiophenes asymmetrically endcapped with solubilizing triarylamine or triarylamino-substituted carbazole dendron and dicyanovinyl groups blended with PCBM as an acceptor showed a PCE up to 1.72% with $V_{oc}$=0.79 V in an as-fabricated device. In addition, the bulk heterojunction PV cells fabricated from dicyanovinyl-substituted dendrimers blended with $PC_{71}BM$ as an acceptor showed a power conversion efficiency up to 1.64% with an open circuit voltage of $(V_{oc})$=0.93 V in the annealed device.

In this invention, the design and synthesis of several novel solution-processable, p-type and low-optical-gap oligothiophene compounds for use in solar cell application are embodied. Specifically, the compounds comprise at least one thiophene-containing group, at least one electron-withdrawing group comprises at least one cyanovinyl group; and at least one electron-donating group; wherein the at least one electron-donating group is selected from a group consisting of diphenylaminofluorenyl group, N-alkylcarbazole group, and a mixture thereof.

Preferably, the at least one cyanovinyl group is selected from a group consisting of dicyanovinyl group, tricyanovinyl group, and a mixture thereof. The structures and preparation procedures of a number of embodied compounds are shown as follows.

EXPERIMENTAL PROCEDURES

Example 1

Compound 1

PhN—OF(2)OT(n)-TCN)

Example 1 embodies an oligothiophene-containing compound (Compound 1, PhN—OF(2)OT(2)-TCN and PhN—OF(2)OT(3)-TCN) comprising a diphenylamino-bisfluorenyl group as the electron-donating group and a tricyanovinyl group as the electron-withdrawing group, wherein n of the thiophene group is selected from a range of 2 to 3

The synthesis of Compound 1 is outlined in Scheme 1. Under a basic condition, 2,7-dibromofluorene was converted to a double alkylation product 9,9-bis-(n-butyl)-2,7-dibromofluorene 1, in a high yield (92%). After Buchwald-Hartwig amination of 1, 2 was converted to boronic acid 3 by means of lithiation followed by reacting with trimethylborate and then hydrolysis. Suzuki cross-coupling reaction of boronic acid 3 and 9,9-bis-(n-butyl)-2,7-dibromofluorene 1 afforded PhN—OF(2)-Br 4 in a good yield, which was then converted to boronic acid, $R_2$—$B(OH)_2$ using a similar method. Palladium catalyzed Suzuki cross-coupling reaction of $R_2$—$B(OH)_2$ and 5-iodo-2,2'-bithiophene (*J. Phys. Chem. C* 2008, 112, 16714-16720) afforded the key intermediate 5a as a yellow solid in 86% yield, which subsequently reacted with n-BuLi and tetracyanoethylene affording the product, PhN—OF(2)OT(2)-TCN in a high yield. In a similar fashion, the extended intermediate 5b was synthesized using the same reaction sequence which was then converted to the second target molecule PhN—OF(2)OT(3)-TCN in a good yield.

Scheme 1 Synthetic routes of PhNOF(2)—OT(*n*)—TCN (n = 2-3).

2 → 3

4

$R_2$—B(OH)$_2$ n = 2; 5a
n = 3; 5b n = 2: PhNOF(2)—OT(2)—TCN
n = 3: PhNOF(2)—OT(3)—TCN

Reagents and conditions: a) n-C$_4$H$_9$Br, KOH, DMF, 90° C., overnight, 80%; b) diphenylamine, NaOBu-t, toluene, 110° C., 24 h, 76%; c) (i) n-BuLi, THF, -78° C., 1 h; (ii) B(OCH$_3$)$_3$, -78° C. to rt, 2 h, 79%; d) Pd(PPh$_3$)$_4$, 2M K$_2$CO$_3$, 80° C., 62%; e) (i) n-BuLi, THF, -78° C., 1 h; (ii) B(OCH$_3$)$_3$, -78° C. to rt, 2 h, 72%. f) Pd(PPh$_3$)$_4$, 2M K$_2$CO$_3$, THF, 5a (n = 2), 76%; 5b (n = 3), 75%; g) 1) n-BuLi 2) tetracyanoethylene, PhN—OF(2)OT(2)—TCN, 90%; PhN—OF(2)OT(3)—TCN, 79%.

Example 2

(PhN—OFFT—TCN)

Compound 2

Example 2 embodies an oligothiophene-containing compound (Compound 2, PhN—OFFT-TCN) comprising a diphenylaminofluorenyl group as the electron-donating group and a tricyanovinyl group as the electron-withdrawing group.

Compound 2 was synthesized as shown in Scheme 2. Under acid condition, dithieno[3,2-b:2',3'-d]thiophene (*Organic Syntheses*, Vol. 83, p. 209 (2006)) was reacted with NBS affording 2-bromodithieno[3,2-b:2',3'-d]thiophene 7, which underwent Suzuki cross-coupling reaction with boronic acid $R_1$—$B(OH)_2$ (*J. Mater. Chem.*, 2010, 20, 2182-2189) to afford intermediate 8 in 71% yields. Finally 8 was converted to PhN—OFFT-TCN by reacting with n-BuLi and tetracyanoethylene at low temperature in 85% yield.

Scheme 2 Synthetic route of PhN—OFFT—TCN.

PhN—OFFT—TCN

Reagents and conditions: a) NBS, CHCl₃/AcOH, 74%; b) 5-4, Pd(PPh₃)₄, 2M K₂CO₃, THF, 71%; c) 1) n-BuLi, 2) tetracyanoethylene, 85%.

Example 3

(ADDA-1)

Compound 3-1

(ADDA-2)

Compound 3-2

Example 3 embodies oligothiophene-containing compounds (Compound 3-1, ADDA-1 and Compound 3-2, ADDA-2), each comprising two diphenylaminofluorenyl groups as the electron-donating groups and two dicyanovinyl groups as the electron-withdrawing groups, wherein n of each of the fluorenyl group is independently selected from a range of 1 to 2.

The structure design of Compound 3-1 and Compound 3-2 is based on the twisted bithiophene skeleton due to the steric effects. (*J. Adv. Funct. Mater.* 2007, 17, 1163). The incorporation of bulky groups at the 3- and 3'-positions of bithiophene could produce a dihedral angle between the thiophene rings, thus generating a nonplanar core for the construction of these compounds.

Scheme 3 outlines the synthetic route for ADDA-1 $_{(n=1)}$ and ADDA-2 $_{(n=2)}$. Palladium-catalysed Kumada coupling reaction of freshly prepared Grignard reagent of 2-bromothiophene in dry tetrahydrofuran (THF) with 2-bromothiophene afforded bithiophene 9 in high yields. Exhaustive bromination of bithiophene with bromine (Br$_2$) in an acid condition gave 3,3',5,5'-tetrabromo-2,2'-bithiophene 10 in 78% yield. Reduction of 10 using Zn/AcOH in aqueous hydrochloric acid (HCl) afforded the desired 3,3'-dibromo-2,2'-bithiophene 11 as a colorless crystal in an high yield. Palladium catalyzed Suzuki cross-coupling reaction of arylboronic acids R$_1$—B(OH)$_2$ or R$_2$—B(OH)$_2$ with 3,3'-dibromo-2,2'-bithiophene afforded the corresponding "double-donor" intermediates 12a or 12b, respectively. Following the typical protocol used previously, donor-substituted intermediates, 12a was converted to diboronic acid 13a in good yields. Without further purification, Suzuki cross-coupling of 13a with iodo-terthiophenecarboxaldehyde afforded the corresponding desired donor-substituted oligothiophenecarboxaldehyde 14a in good yields. Lastly, 14a was converted to ADDA-1 $_{(n=1)}$ by reacting with malononitrile in the presence of pyridine in chloroform (CHCl$_3$) under nitrogen (N$_2$). ADDA-2 $_{(n=2)}$ was also prepared according to similar procedure.

Scheme 3 Synthetic routes of ADDA-1 and ADDA-2.

Reagents and conditions: a) Br$_2$, CHCl$_3$/AcOH, 76%, b) Zn, AcOH, 3M HCl, C$_2$H$_5$OH, H$_2$O, 95%; c) Pd(PPh$_3$)$_4$, 2M K$_2$CO$_3$, THF, 12a, 71%; 12b, 70%; d) 1) n-BuLi, 2) B(OCH$_3$)$_3$, 13a, 70%; 13b, 68%; e) Pd(PPh$_3$)$_4$, 2M K$_2$CO$_3$, THF, 14a, 68%;, 14b, 73%; f) malononitrile, pyridine, CHCl$_3$, overnight, ADDA-1, 93%; ADDA-2, 90%.

Example 4

Example 4 embodies an oligothiophene-containing compound (Compound 4, ADDA-3) comprising two N-alkylcarbazole groups as the electron-donating groups and two dicyanovinyl groups as the electron-withdrawing groups.

ADDA-3 was synthesized according to Scheme 4.

Scheme 4 Synthetic routes of ADDA-3.

ADDA-3

Reagents and conditions: a) n-$C_{10}H_{21}$, 50% NaOH, benzene, 90%; b) NBS, $CH_2Cl_2$, 87%; c) 1) n-BuLi, 2) B(OCH$_3$)$_3$, 80%; d) Pd(PPh$_3$)$_4$, 2M K$_2$CO$_3$, THF, 75%; e) 1) n-BuLi, 2) B(OCH$_3$)$_3$, 72%; f) Pd(PPh$_3$)$_4$, 2M K$_2$CO$_3$, THF, 73%; g) malononitrile, pyridine, CHCl$_3$, overnight, ADDA-3, 95%.

Characterizations and Results

All of the newly synthesized oligothiophenes were fully characterized by $^1$H NMR, $^{13}$C NMR, HRMS and found to be in good agreement with expected structures.

9,9-Bis-(n-butyl)-2,7-dibromofluorene (1). A mixture of 12.0 g (37 mmol) of 2,7-dibromofluorene 2-7, 12 mL (111 mmol) of 1-bromobutane, 6.3 g (1 mmol) of potassium hydroxide, 0.9 g (6 mmol) of potassium iodide, 0.29 g (1 mmol) of 18-crown-6 and 120 mL of DMF was stirred and heated to 90° C. for overnight under $N_2$. After cooling to room temperature, the solution was poured to cold water and extracted with dichloromethane (3×50 mL). The combined organic layer was washed with water, dried over anhydrous NaSO$_4$, filtered and evaporated to dryness. The crude product was purified by silica gel column chromatography using petroleum ether as eluent affording the desired product as a white solid (12.9 g, 80%). Mp: 116.8-118.5° C. $^1$H NMR (400 MHz, CDCl$_3$, δ) 7.53 (d, J=8.8 Hz, 2H), 7.46 (dd, J=7.2 Hz, J=2.2 Hz, 4H), 1.90-1.94 (m, 4H), 1.06-1.11 (m, 4H), 0.70 (t, J=7.4 Hz, 3H), 0.54-0.59 (m, 4H). $^{13}$C NMR (100 MHz, CDCl$_3$, δ) 152.5, 139.1, 130.2, 126.2, 121.5, 121.2, 55.6, 40.1, 25.8, 22.9, 13.8. MS (FAB) m/z 436.1 (M$^+$).

9,9-Bis(n-butyl)-7-bromo-2-diphenylaminofluorene (2). To a two-neck round-bottom flask was added 1.69 g (10 mmol) of diphenylamine, 4.36 g (10 mmol) of 9,9-bis(n-butyl)-2,7-dibromofluorene 1, 100 mg (0.5 mmol) of Pd(OAc)$_2$, 250 mg (1 mmol) of P(o-tol)$_3$, 3.0 g (30 mmol) of NaOBu-t and 80 mL of toluene. The mixture was stirred and heated to 110° C. for 36 h under $N_2$. After cooling to room temperature, the solution was poured to cold water and extracted with ethyl acetate (3×80 mL). The combined organic layer was washed with water, dried over anhydrous sodium sulfate, filtered and evaporated to dryness. The crude product was purified by silica gel column chromatography using petroleum ether/dichloromethane as eluent affording the desired product as a white solid (3.95 g, 76%). Mp: 116.0-118.0° C. $^1$H NMR (400 MHz, CDCl$_3$, δ) 7.40-7.52 (m, 4H), 7.22-7.27 (m, 4H), 7.08-7.13 (m, 5H), 6.99-7.03 (m, 3H) 1.80-1.85 (m, 4H), 1.02-1.08 (m, 4H), 0.70 (t, J=7.4 Hz, 6H), 0.59-0.67 (m, 4H). $^{13}$C NMR (100 MHz, CDCl$_3$, δ) 152.8, 151.7, 147.8, 147.5, 139.9, 134.9, 129.9, 129.2, 125.9, 123.9, 123.3, 122.6, 120.4, 120.3, 120.1, 118.9, 55.2, 39.9, 25.9, 22.9, 13.9. MS (FAB) m/z 524.4 (M$^+$+1).

9,9-Bis(n-butyl)-2-diphenylamino-7-fluorenylboronic acid (3). To a dry 100 mL two-neck flask containing 1.3 g (2.47 mmol) of compound 2 and 30 mL of dry THF was dropwise added 2.3 mL (3.71 mmol) of 1.6 M of n-butyl lithium under $N_2$ at −78° C. while maintaining a good stirring. After stirring for 1 h, trimethyl borate (0.4 mL, 3.71 mmol) was added in one portion. The reaction mixture was stirred for 1 h at −78° C. When the mixture was naturally warmed to −30° C., water and HCl (3 M) were added. Then the solution mixture was poured into water wad extracted with ethyl acetate (3×50 mL). The combined organic phase was dried over anhydrous sodium sulfate, filtered and evaporated to dryness under 35° C. The crude product was purified by silica gel column chromatography using dichloromethane and petroleum ether/ethyl acetate as eluent affording a light-yellow solid (0.96 g, 79%). $^1$H NMR (400 MHz, DMSO-$d_6$, δ) 8.02 (s, 2H), 7.80 (s, 1H), 7.77 (d, J=7.6 Hz, 1H), 7.71 (d, J=8.4 Hz, 1H), 7.27 (t, J=7.6 Hz, 1H), 7.08 (d, J=1.6 Hz, 1H), 6.93-7.01 (m, 6H), 6.91 (d, J=2.0 Hz, 1H), 1.79-1.88 (m, 4H), 0.95-1.04 (m, 4H), 0.65 (t, J=7.4 Hz, 6H), 0.50-0.58 (m, 4H). $^{13}$C NMR (100 MHz, DMSO-$d_6$, δ) 152.1, 148.9, 147.4, 146.8, 142.1, 136.1, 133.1, 129.4, 129.3, 128.2, 123.3, 122.7, 121.1, 119.1, 118.3, 54.3, 39.2, 25.8, 22.4, 13.8. MS (FAB) m/z 489.7 ($M^+$).

PhN—OF(2)-Br (4). To a 100 mL round-bottom flask was added 250 mg (0.51 mmol) of boronic acid 3, 300 mg (0.69 mmol) of 9,9-bis(n-butyl)-2,7-dibromofluorene 1, 50 mg of Pd(PPh$_3$)$_4$, 4 mL of 2 M K$_2$CO$_3$, 5 mL of toluene and 8 mL of CH$_3$OH. The mixture was stirred and heated to 80° C. for overnight under N$_2$. After cooling to room temperature, the mixture was poured into water and extracted with dichloromethane (3×20 mL). The combined organic phase was dried over anhydrous sodium sulfate, filtered and evaporated to dryness. The crude product was purified by silica gel column chromatography using petroleum ether/dichloromethane as eluent affording the desired product as a little-yellow solid (253 mg, 62%). Mp: 186.0-188.0° C. $^1$H NMR (400 MHz, CDCl$_3$, δ) 7.58-7.70 (m, 8H), 7.23-7.38 (m, 6H), 7.13-7.15 (m, 5H), 6.99-7.05 (m, 3H). $^{13}$C NMR (100 MHz, CDCl$_3$, δ) 152.4, 151.4, 151.3, 150.9, 147.9, 147.1, 140.8, 140.4, 140.1, 139.6, 135.9, 129.1, 126.9, 126.8, 125.9, 125.8, 123.8, 123.5, 122.9, 122.5, 121.2, 120.4, 119.9, 119.7, 119.4, 119.3, 55.1, 40.2, 39.9, 26.1, 25.9, 23.1, 23.0, 13.9, 13.8. MS (MALDI-TOF): m/z 801.8 ($M^+$).

PhN—OF(2)OT(2) (5a). To a 100 two-neck round-bottom flask was added R$_2$—B(OH)$_2$ (460 mg, 0.6 mmol), 5-indo-2,2'-bithiophene (2-5) (147 mg, 0.5 mmol), Pd(PPh$_3$)$_4$ (20 mg), THF (20 mL) and 2 M K$_2$CO$_3$ (1.2 mL). The solution mixture was heated to 80° C. overnight under N$_2$. After cooling to room temperature, the reaction mixture was poured into water and extracted with dichloromethane (3×30 mL). The combined organic phase was dried over anhydrous Na$_2$SO$_4$ and evaporated to dryness. The crude product was purified by silica gel column chromatography using petroleum ether/dichloromethane as eluent affording the desired product as a yellow solid (336 mg, 76%). $^1$H NMR (400 MHz, CDCl$_3$, δ) 7.78-7.57 (m, 10H), 7.32 (d, J=3.6 Hz, 1H), 7.28-7.22 (m, 6H), 7.19 (d, J=3.6 Hz, 1H), 7.16-7.13 (m, 5H), 7.06-6.99 (m, 4H), 2.09-1.86 (m, 8H), 1.16-1.08 (m, 8H), 0.75-0.68 (m, 20H). $^{13}$C NMR (100 MHz, CDCl$_3$, δ) 152.4, 151.8, 151.6, 151.4, 147.9, 147.1, 143.9, 140.6, 140.2, 139.7, 139.5, 137.5, 136.3, 135.9, 132.7, 129.1, 127.9, 126.0, 125.9, 124.6, 124.5, 124.3, 123.8, 123.5, 123.4, 122.5, 121.2, 121.1, 120.4, 120.1, 119.9, 119.8, 119.3, 55.2, 55.1, 40.3, 39.9, 26.1, 26.0, 23.1, 23.0, 13.9, 13.8. MS (MALDI-TOF): m/z 885.7902 ($M^+$).

PhN—OF(2)OT(3) (5b). The synthetic procedure of 5a was followed using R$_2$—B(OH)$_2$ (380 mg, 0.5 mmol), 5-iodo-2,2':5',2''-terthiophene (150 mg, 0.4 mmol), Pd(PPh$_3$)$_4$ (20 mg), THF (20 mL) and 2M K$_2$CO$_3$ (1.0 mL). The crude product was purified by silica gel column chromatography using petroleum ether/dichloromethane as eluent affording the desired product as a yellow solid (290 mg, 75%). $^1$H NMR (400 MHz, CDCl$_3$, δ) 7.78-7.57 (m, 10H), 7.32 (d, J=3.6 Hz, 1H), 7.28-7.21 (m, 6H), 7.19-7.17 (m, 2H), 7.16-7.10 (m, 7H), 7.06-6.99 (m, 4H), 2.10-1.86 (m, 8H), 1.16-1.06 (m, 8H), 0.75-0.68 (m, 20H). $^{13}$C NMR (100 MHz, CDCl$_3$, δ) 152.4, 151.8, 151.6, 151.4, 147.9, 147.1, 144.0, 140.6, 140.5, 140.2, 139.6, 139.5, 137.1, 136.3, 136.1, 135.9, 135.8, 132.6, 129.1, 127.9, 126.1, 125.9, 124.6, 124.5, 124.4, 124.1, 123.8, 123.7, 123.6, 123.5, 122.5, 121.2, 121.1, 120.4, 120.1, 119.9, 119.8, 119.3, 55.2, 55.1, 40.3, 39.9, 26.1, 26.0, 23.1, 23.0, 13.9, 13.8. MS (MALDI-TOF): m/z 996.8428 ($M^+$).

PhN—OF(2)OT(2)-TCN. To a dry 50 mL two-neck flask containing 5a (284 mg, 0.32 mmol) and dry THF (20 mL) was dropwise added 1.6 M of n-butyl lithium (0.4 mL, 0.64 mmol) under N$_2$ at −78° C. while maintaining a good stirring. After stirring for 2 h at −78° C., tetracyanoethylene (128 mg, 1.0 mmol) was added in one portion, and then the mixture was stirred for another 0.5 h at −78° C. and allowed to warm to room temperature for 1 h. Then the reaction mixture was quenched with H$_2$O and poured into water, extracted with dichloromethane (2×100 mL). The combined organic phase was dried with anhydrous sodium sulfate, and evaporated to dryness. The crude product was then loaded on silica gel column and eluted with petroleum ether/dichloromethane affording a black solid which was further purified by precipitation with CHCl$_3$/CH$_3$OH, washed with methanol and dried in vacuum affording the desired product as a blue-black solid (284 mg, 90%). $^1$H NMR (400 MHz, CDCl$_3$, δ) 8.04 (d, J=4.8 Hz, 1H), 7.81 (dd, J=9.4 Hz, J=7.8 Hz, 2H), 7.72-7.57 (m, 9H), 7.47 (d, J=4.0 Hz, 1H), 7.42 (d, J=4.4 Hz, 1H), 7.29-7.25 (m, 4H), 7.17-7.14 (m, 5H), 7.07-7.01 (m, 3H), 2.13-1.89 (m, 8H), 1.18-1.09 (m, 8H), 0.76-0.70 (m, 20H). $^{13}$C NMR (100 MHz, CDCl$_3$, δ) 152.6, 152.4, 152.2, 151.8, 151.5, 150.9, 147.9, 147.2, 142.3, 141.7, 141.3, 140.4, 139.3, 139.2, 135.8, 132.9, 131.9, 131.6, 131.3, 130.1, 129.2, 126.3, 126.0, 125.2, 125.0, 124.9, 123.9, 123.5, 122.5, 121.3, 121.2, 120.4, 120.3, 120.2, 119.4, 119.3, 112.8, 112.7, 112.3, 80.7, 55.4, 55.1, 40.2, 39.9, 26.1, 26.0, 23.03, 23.01, 13.9, 13.8. HRMS (MALDI-TOF): calcd: For C$_{62}$H$_{62}$N$_4$S$_2$: 986.4410. Found: 986.4448.

PhN—OF(2)OT(3)-TCN. The synthetic procedure of PhN—OF(2)OT(2)-TCN was followed using 5b (242 mg, 0.25 mmol), 1.6 M of n-butyl lithium (0.4 mL, 0.64 mmol), tetracyanoethylene (128 mg, 1.0 mmol) and dry THF (20 mL). The crude product was then loaded on silica gel column chromatography and eluted with petroleum ether/dichloromethane affording a black solid which was further purified by precipitation with CHCl$_3$/CH$_3$OH, washed with methanol and dried in vacuum affording the desired product as a blue-black solid (210 mg, 79%). $^1$H NMR (400 MHz, CDCl$_3$, δ) 8.02 (d, J=4.4 Hz, 1H), 7.80 (dd, J=9.4 Hz, J=7.8 Hz, 2H), 7.72-7.60 (m, 8H), 7.50 (d, J=4.0 Hz, 1H), 7.38 (d, J=3.6 Hz, 1H), 7.36 (d, J=4.4 Hz, 1H), 7.33 (d, J=4.0 Hz, 1H), 7.29-7.25 (m, 5H), 7.17-7.14 (m, 5H), 7.07-7.00 (m, 3H), 2.12-1.87 (m, 8H), 1.18-1.09 (m, 8H), 0.76-0.70 (m, 20H). $^{13}$C NMR (100 MHz, CDCl$_3$, δ) 152.4, 152.0, 151.7, 151.4, 147.9, 147.2, 146.7, 143.1, 141.6, 141.4, 140.9, 140.3, 139.40, 139.37, 135.8, 134.4, 132.5, 132.0, 131.9, 131.4, 130.0, 129.2, 126.6, 126.2, 126.0, 125.1, 125.0, 124.8, 124.0, 123.8, 123.5, 122.5, 121.3, 121.2, 120.4, 120.3, 120.1, 119.9, 119.3, 112.7, 112.6, 112.3, 80.8, 55.3, 55.1, 40.2, 39.9, 26.1, 26.0, 23.1, 23.0, 13.9, 13.8. HRMS (MALDI-TOF): calcd: For C$_{21}$H$_{64}$N$_4$S$_3$: 1068.4287. Found: 1068.4245.

2-Bromodithieno[3,2-b:2',3'-d]thiophene (7). To a mixture of 6[2] (196 mg, 1.0 mmol) and AcOH (20 mL)/CHCl$_3$ (20 mL) was added N-bromosuccinimide (178 mg, 1.0 mmol) in portion at 0° C. The mixture was stirred overnight, and then poured to H$_2$O (150 mL) and extracted with dichloromethane (3×30 mL). The combined organic extract was washed with brine, water and then dried over anhydrous Na$_2$SO$_4$. After removal of solvent, the residue was purified by silica gel column chromatography using petroleum ether as eluent affording the desired product as a colorless liquid (203 mg, 74%). $^1$H NMR (400 MHz, CDCl$_3$, δ) 7.38 (d, J=5.2 Hz, 1H), 7.29-7.27 (m, 2H). $^{13}$C NMR (100 MHz, CDCl$_3$, δ) 140.7, 139.8, 131.1, 130.7, 126.2, 123.4, 120.6, 111.9. MS (FAB): m/z (M$^+$).

PhN—OFFT (8). To a 100 mL two-neck round-bottom flask was added R$_1$—B(OH)$_2$$^3$, (330 mg, 0.5 mmol), 7 (110 mg, 0.4 mmol), Pd(PPh$_3$)$_4$ (20 mg), THF (30 mL) and 2M K$_2$CO$_3$ (1.0 mL). The solution mixture was heated to 80° C. overnight under N$_2$. After cooling to room temperature, the reaction mixture was poured into water and extracted with dichloromethane (3×50 mL). The combined organic phase was dried over anhydrous Na$_2$SO$_4$ and evaporated to dryness. The crude product was purified by silica gel column chromatography using petroleum ether/dichloromethane as eluent affording the desired product as a yellow liquid (230 mg, 71%). $^1$H NMR (400 MHz, CDCl$_3$, δ) 7.65-7.56 (m, 5H), 7.38 (d, J=5.2 Hz, 1H), 7.32 (d, J=5.2 Hz, 1H), 7.29-7.25 (m, 4H), 7.16-7.13 (m, 5H), 7.05-7.01 (m, 3H), 1.97-1.82 (m, 4H), 1.19-1.08 (m, 28H), 0.87 (t, J=6.8 Hz, 6H), 0.73-0.69 (m, 4H). $^{13}$C NMR (100 MHz, CDCl$_3$, δ) 152.3, 151.6, 147.9, 147.3, 145.9, 142.2, 140.96, 140.91, 135.5, 132.5, 131.2 129.6, 129.2, 125.8, 124.7, 123.9, 123.5, 122.6, 120.8, 120.5, 119.7, 119.6, 119.2, 116.1, 55.1, 40.2, 31.9, 29.9, 29.6, 29.5, 29.3, 23.8, 22.6, 14.1. MS (MALDI-TOF): m/z 806.7590 (M$^+$).

PhN—OFFT-TCN. The synthetic procedure of PhN—OF (2)OT(2)-TCN was followed using 8 (200 mg, 0.25 mmol), 1.6 M of n-butyl lithium (0.4 mL, 0.64 mmol), tetracyanoethylene (128 mg, 1.0 mmol) and dry THF (20 mL). The crude product was then loaded on silica gel column and eluted with petroleum ether/dichloromethane affording a black solid which was further purified by precipitation with CHCl$_3$/CH$_3$OH, washed with methanol and dried in vacuum affording the desired product as a blue-black solid (193 mg, 85%). $^1$H NMR (400 MHz, CDCl$_3$, δ) 8.27 (s, 1H), 7.68-7.63 (m, 3H), 7.59-7.57 (m, 2H), 7.29-7.25 (m, 4H), 7.16-7.07 (m, 5H), 7.07-7.03 (m, 3H), 1.98-1.83 (m, 4H), 1.25-1.08 (m, 28H), 0.85 (t, J=6.8 Hz, 6H), 0.71-0.68 (m, 4H). $^{13}$C NMR (100 MHz, CDCl$_3$, δ) 155.2, 152.6, 151.9, 151.6, 148.1, 147.8, 143.1, 142.6, 142.4, 134.7, 133.9, 132.6, 131.9, 130.8, 129.2, 128.7, 125.5, 124.2, 123.2, 122.9, 120.9, 120.2, 119.8, 118.6, 116.3, 112.9, 112.8, 112.4, 79.8, 55.3, 40.2, 31.9, 29.9, 29.5, 29.3, 23.9, 22.6, 14.1. HRMS (MALDI-TOF): calcd: For C$_{58}$H$_{60}$N$_4$S$_3$: 908.3974. Found: 908.3945.

3,3',5,5'-tetrabromo-2,2'-bithiophene (10). To a solution of 2,2'-bithiophene (8.3 g, 50 mmol) in a mixed solvent of glacial acetic acid (35 mL) and chloroform (70 mL) at 5-15° C. was added bromine (32.0 g, 200 mmol) dropwise over 1.5 h. The solution mixture was subsequently stirred at room temperature for 5 h and then under reflux for 24 h. After cooling to room temperature, the reaction was quenched by an addition of 80 mL of 10% KOH aqueous solution. The mixture was extracted with CHCl$_3$ (2×100 mL). The combined extract was washed with water, dried over anhydrous MgSO$_4$, filtered, and the solvent removed by evaporation. The residual solid was recrystallized from ethanol affording the desired product as off-white crystals (18.8 g, 78%). $^1$H NMR (400 MHz, CDCl$_3$, δ) 7.06 (s, 2H). $^{13}$C NMR (100 MHz, CDCl$_3$, δ) 132.9, 129.5, 114.8, 112.1. MS (FAB): m/z 481.0 (M$^+$).

3,3'-dibromo-2,2'-bithiophene (11). 3,3',5,5'-Tetrabromo-2,2'-bithiophene, 10 (15 g, 31.1 mmol) was added in portion within 0.5 h to a refluxing dispersion of zinc powder (7.8 g, 0.12 mol) in 150 mL of ethanol containing 15 mL of water, 72 mL of glacial acetic acid, and 3.1 mL of 3 M HCl. After refluxing for an additional 2 h and then cooling to room temperature, the mixture was filtered and washed three times with ethanol, and the filtrate was collected. The solvent was then removed by evaporation, and 60 mL of H$_2$O was added. The mixture was then extracted with dichloromethane (3×100 mL), and the combined extract was washed with water, dried over anhydrous MgSO$_4$, and filtered. The solvent was removed by evaporation, and the crude product was crystallized from hexane to give colorless crystals of product 9.2 g, 92% yield. $^1$H NMR (400 MHz, CDCl$_3$, δ) 7.43 (d, J=5.4 Hz, 2H), 7.09 (d, J=5.4 Hz, 2H). $^{13}$C NMR (100 MHz, CDCl$_3$, δ) 130.8, 128.8, 127.5, 112.6. MS (FAB): m/z 324.0 (M$^+$).

3,3'-Bis[9,9-bis(n-decyl)-2-diphenylamino-7-fluoryl]-2, 2'-bithiophene (12a). To a 100 two-neck round-bottom flask was added R$_1$—B(OH)$_2$, (790 mg, 1.2 mmol), 11 (162 mg, 0.5 mmol), Pd(PPh$_3$)$_4$ (50 mg), THF (30 mL) and 2M K$_2$CO$_3$ (2.4 mL). The solution mixture was heated to 80° C. overnight under N$_2$. After cooling to room temperature, the reaction mixture was poured into water and extracted with dichloromethane (3×30 mL). The combined organic phase was dried over anhydrous Na$_2$SO$_4$ and evaporated to dryness. The crude product was purified by silica gel column chromatography using petroleum ether/dichloromethane as eluent affording the desired product as a colorless oil liquid (583 mg, 84%). $^1$H NMR (400 MHz, CDCl$_3$, δ) 7.53 (d, J=8.4 Hz, 2H), 7.49 (d, J=8.0 Hz, 2H), 7.39 (d, J=5.2 Hz, 2H), 7.28-7.23 (m, 10H), 7.19-7.08 (m, 14H), 7.04-6.99 (m, 6H), 1.74-1.62 (m, 8H), 1.29-1.01 (m, 56H), 0.90 (t, J=7.0 Hz, 12H), 0.57-0.55 (m, 8H). $^{13}$C NMR (100 MHz, CDCl$_3$, δ) 152.3, 150.5, 147.9, 146.9, 142.2, 139.6, 136.1, 133.8, 129.6, 129.1, 128.9, 127.0, 125.9, 123.7, 123.5, 122.7, 122.4, 120.3, 119.4, 118.8, 54.8, 40.3, 31.9, 30.1, 29.7, 29.6, 29.4, 29.3, 23.8, 22.7, 14.1. MS (MALDI-TOF): m/z 1389.1621 (M$^+$).

4,4'-Bis[9,9-bis(n-decyl)-2-diphenylamino-7-fluoryl]-2, 2'-di(2,2':5',2"-terthiophene-5"-carboxaldehyde)-5,5'-bithiophene (14a). To a 100 two-neck round-bottom flask was added 4,4'-Bis[9,9-bis(n-decyl)-2-diphenylamino-7-fluoryl]-5,5'-bithiophene-2,2'-diboronic acid 13a (372 mg, 0.25 mmol), which was prepared from 12a (486 mg, 0.35 mmol), 1.6 M n-BuLi (0.9 mL, 1.4 mmol) and trimethyl borate (0.2 mL, 2 mmol) using a typical procedure, 5-iodo-2,2':5',2"-terthiophene-5"-carboxaldehyde, (242 mg, 0.6 mmol), Pd(PPh$_3$)$_4$ (25 mg), THF (20 mL) and 2M K$_2$CO$_3$ (0.5 mL). The solution mixture was heated to 80° C. overnight under N$_2$. After cooling to room temperature, the reaction mixture was poured into water and extracted with dichloromethane (3×30 mL). The combined organic phase was dried over anhydrous Na$_2$SO$_4$ and evaporated to dryness. The crude product was purified by silica gel column chromatography using petroleum ether/dichloromethane as eluent affording the desired product as a red solid (390 mg, 80%). $^1$H NMR (400 MHz, CDCl$_3$, δ) 9.87 (s, 2H), 7.69 (d, J=8.0 Hz, 2H), 7.55-7.51 (m, 4H), 7.29-7.19 (m, 18H), 7.13-7.07 (m, 16H), 7.03-6.99 (m, 6H), 1.76-1.66 (m, 8H), 1.24-0.97 (m, 56H), 0.85 (t, J=7.0 Hz, 12H), 0.63-0.57 (m, 8H). $^{13}$C NMR (100 MHz, CDCl$_3$, δ) 182.4, 152.3, 150.7, 147.9, 147.1, 146.6, 143.5, 141.6, 140.2, 138.7, 137.4, 137.0, 136.6, 135.8, 135.4, 134.6, 133.2, 129.1, 128.3, 127.0, 126.9, 125.6, 125.1, 124.7, 124.6, 124.0, 123.8, 123.4, 122.9, 122.4, 120.4, 119.3, 119.0, 54.8, 40.2, 31.9, 30.1, 29.8, 29.7, 29.5, 29.4, 23.9, 22.7, 14.1. MS (MALDI-TOF): m/z 1937.8069 (M$^+$).

ADDA-1. To a 100 mL round-bottom flask containing 14a (300 mg, 0.15 mmol) and chloroform (20 mL) was added malononitrile (0.40 g, 6.1 mmol) and pyridine (0.8 mL) at room temperature. The solution mixture was stirred and heated to reflux overnight under N$_2$. After cooling to room temperature, the reaction mixture was poured into water, neutralized with 0.1M HCl, and extracted with CHCl$_3$ (3×30 mL). The combined organic phase was washed with water, dried over anhydrous $Na_2SO_4$, filtered and evaporated to dryness. The residual solid was purified by silica gel column chromatograph using petroleum ether/dichloromethane as eluent affording a black red solid which was further purified by precipitation with $CHCl_3/CH_3OH$, washed with $CH_3OH$ and dried in vacuo affording the desired product as a black solid (284 mg, 93%). $^1$H NMR (400 MHz, $CDCl_3$, δ) 7.67 (s, 2H), 7.55 (d, J=4.4 Hz, 2H), 7.45-7.41 (m, 4H), 7.27 (d, J=3.6 Hz, 2H), 7.20-7.09 (m, 14H), 7.06-6.98 (m, 16H), 6.93-6.89 (m, 6H), 1.66-1.54 (m, 8H), 1.14-0.86 (m, 56H), 0.75 (t, J=7.0 Hz, 12H), 0.51-0.49 (m, 8H). $^{13}$C NMR (100 MHz, $CDCl_3$, δ) 152.3, 150.7, 149.9, 148.8, 147.9, 147.2, 143.6, 140.2, 140.14, 140.11, 137.2, 136.9, 135.7, 135.1, 133.6, 133.4, 133.1, 129.1, 128.5, 128.1, 127.1, 125.8, 125.6, 124.9, 124.8, 124.3, 123.8, 123.4, 122.9, 122.5, 120.4, 119.3, 119.1, 114.3, 113.5, 76.0, 54.9, 40.2, 31.9, 30.1, 29.8, 29.7, 29.5, 29.4, 23.9, 22.7, 14.1. HRMS (MALDI-TOF): calcd: For $C_{130}H_{132}N_6S_8$: 2033.8316. Found: 2033.8320.

3,3'-Bis{2-diphenylamino-7,7'-di[9,9-Bis(n-butyl)fluorene]-2"-yl}-2,2'-bithiophene (12b). The synthetic procedure of 12a was followed using $R_2$—$B(OH)_2$ (940 mg, 1.23 mmol), 11 (162 mg, 0.5 mmol), $Pd(PPh_3)_4$ (40 mg), THF (30 mL) and 2M $K_2CO_3$ (2.4 mL). The crude product was purified by silica gel column chromatography using petroleum ether/dichloromethane as eluent affording the desired product as a colorless oil liquid (570 mg, 71%). $^1$H NMR (400 MHz, $CDCl_3$, δ) 7.72-7.56 (m, 16H), 7.42 (d, J=5.2 Hz, 2H), 7.27-7.23 (m, 14H), 7.15-7.13 (m, 10H), 7.05-6.99 (m, 6H), 2.00-1.74 (m, 16H), 1.14-0.98 (m, 16H), 0.74-0.56 (m, 40H). $^{13}$C NMR (100 MHz, $CDCl_3$, δ) 152.4, 151.7, 151.4, 150.9, 147.9, 147.1, 142.3, 140.3, 140.1, 139.9, 139.6, 134.5, 129.8, 129.1, 129.0, 127.1, 126.1, 125.9, 125.8, 123.8, 123.5, 123.0, 122.5, 121.2, 120.3, 119.9, 119.5, 119.4, 119.3, 55.1, 54.9, 40.3, 39.9, 26.1, 25.9, 23.1, 23.0, 13.88, 13.86. MS (MALDI-TOF): m/z 1605.0822 ($M^+$).

4,4'-Bis{2-diphenylamino-7,7'-di[9,9-bis(n-butyl)fluorene]-2"-yl}-2,2'-di(2,2':5',2"-terthiophene-5"-carboxaldehyde)-5,5'-bithiophene (14b). The synthetic procedure of 14a was followed using 13b (395 mg, 0.23 mmol), which was prepared from 12b (500 mg, 0.31 mmol), 1.6 M n-BuLi (0.8 mL, 1.25 mmol) and trimethyl borate (0.2 mL, 2 mmol) using the standard procedure, 5-indo-2,2':5',2"-terthiophene-5"-carboxaldehyde, (242 mg, 0.6 mmol), $Pd(PPh_3)_4$ (25 mg), THF (20 mL) and 2M $K_2CO_3$ (0.5 mL). The crude solid was purified by silica gel column chromatography using petroleum ether/dichloromethane as eluent affording the desired product as a red solid (376 mg, 76%). $^1$H NMR (400 MHz, $CDCl_3$, δ) 9.88 (s, 2H), 7.78-7.59 (m, 18H), 7.35-7.01 (m, 40H), 2.02-1.83 (m, 16H), 1.13-1.02 (m, 16H), 0.76-0.62 (m, 40H). $^{13}$C NMR (100 MHz, $CDCl_3$, δ) 182.4, 152.4, 151.7, 151, 151.1, 147.9, 147.1, 146.6, 143.4, 141.7, 140.5, 140.5, 140.2, 140.1, 139.7, 139.5, 138.7, 137.4, 137.2, 136.6, 135.9, 135.5, 134.7, 133.9, 129.1, 128.4, 127.2, 126.9, 125.9, 125.7, 125.2, 124.8, 124.7, 124.1, 123.8, 123.4, 123.0, 122.5, 121.3, 121.1, 120.4, 120.0, 119.7, 119.3, 55.0, 54.9, 40.2, 39.9, 26.1, 26.0, 23.1, 22.9, 13.9. MS (MALDI-TOF): m/z 2154.8131 ($M^+$).

ADDA-2. The synthetic procedure of ADDA-1 was followed using 14b (300 mg, 0.14 mmol), malononitrile (0.40 g, 6.1 mmol), pyridine (0.8 mL) and $CHCl_3$ (20 mL). The residual solid was purified by silica gel column chromatography using petroleum ether/dichloromethane as eluent affording a black red solid which was further purified by precipitation with $CHCl_3/CH_3OH$, washed with methanol and dried in vacuum affording the desired product as a black solid (270 mg, 86%). $^1$H NMR (400 MHz, $CDCl_3$, δ) 7.76-7.44 (m, 4H), 7.69-7.57 (m, 16H), 7.38 (d, J=4.0 Hz, 2H), 7.33 (s, 4H), 7.29-7.24 (m, 12H), 7.17-7.12 (m, 16H), 7.06-7.01 (m, 6H), 2.01-1.81 (m, 16H), 1.16-0.98 (m, 16H), 0.74-0.61 (m, 40H). $^{13}$C NMR (100 MHz, $CDCl_3$, δ) 152.3, 151.7, 151.4, 151.1, 149.9, 148.8, 147.9, 143.5, 140.5, 140.21, 140.16, 140.07, 139.7, 139.4, 137.12, 137.07, 135.8, 135.2, 133.9, 133.7, 133.5, 129.1, 128.5, 128.2, 127.2, 125.94, 125.84, 125.6, 124.96, 124.87, 124.4, 123.8, 123.4, 123.0, 122.5, 121.3, 121.1, 120.4, 120.0, 119.7, 119.3, 114.3, 113.5, 76.0, 55.0, 54.9, 40.2, 39.9, 26.1, 26.0, 23.1, 22.9, 13.9. HRMS (MALDI-TOF): calcd: For $C_{148}H_{132}N_6S_8$: 2251.0043. Found: 2251.0046.

9-Decylcarbazole (15). To a solution of carbazole (2.1 g, 12.5 mmol), benzene (10 mL), tetrabutylammonium bromine (0.1 g, 0.7 mmol) and 1-bromodecane (3.0 mL, 15 mmol), was added 50% NaOH aqueous solution (15 mL). The solution mixture was heated to 80° C. and stirred for 2 h. The solvent was evaporated in vacuo and the residue was extracted with dichloromethane (3×30 mL). The organic layer was dried over anhydrous $Na_2SO_4$ and filtered. After removal of solvent, the product was purified by silica gel column chromatography using petroleum ether/dichloromethane as eluent affording 9-decylcarbazole as a colorless liquid (3.4 g, 90%). $^1$H NMR (400 MHz, $CDCl_3$, δ) 8.10 (d, J=7.6 Hz, 2H), 7.48-7.38 (m, 4H), 7.24 (dd, J=14.4 Hz, J=1.2 Hz, 2H), 4.30 (t, J=7.2 Hz, 2H), 1.89-1.81 (m, 2H), 1.39-1.23 (m, 14H), 0.88 (t, J=7.0 Hz, 3H). $^{13}$C NMR (100 MHz, $CDCl_3$, δ) 140.4, 125.5, 122.8, 120.3, 118.6, 108.6, 43.1, 31.8, 29.5, 29.48, 29.40, 29.3, 28.9, 27.3, 22.7, 14.1. MS (MALDI-TOF): m/z 307.2579 ($M^+$).

4-Bromo-9-decylcarbazole (16). To a solution of 9-decylcarbazole 15 (3.0 g, 10 mmol) in dichloromethane (90 mL) was added N-bromosuccinimide (1.80 g, 10.1 mmol) at 0° C. in portions. The mixture was warmed to room temperature and stirred overnight. After removal of the solvent, the residue was purified by silica gel column chromatography using petroleum ether/dichloromethane as eluent affording the desired product (3.35 g, 87%). $^1$H NMR (400 MHz, $CDCl_3$, δ) 8.19 (d, J=1.6 Hz, 1H), 8.04 (d, J=8.0 Hz, 1H), 7.53-7.45 (m, 2H), 7.39 (d, J=8.0 Hz, 1H), 7.24-7.20 (m, 2H), 4.26 (t, J=7.2 Hz, 2H), 1.86-1.79 (m, 2H), 1.30-1.22 (m, 2H), 0.88 (t, J=6.4 Hz, 3H). $^{13}$C NMR (100 MHz, $CDCl_3$, δ) 140.7, 139.0, 128.2, 126.3, 124.5, 123.0, 121.8, 120.5, 119.1, 111.5, 110.1, 108.9, 43.2, 31.8, 29.5, 29.4, 29.3, 29.2, 28.9, 27.2, 22.6, 14.1. MS (MALDI-TOF): m/z 387.0912 ($M^+$).

9-Decylcarbazole-4-boronic acid [$R_3$—$B(OH)_2$]. By using the standard procedure, to a dry 100 mL two-neck round-bottom flask containing 4-bromodecylcarbazole 16 (3.86 g, 10 mmol) and dry THF (50 mL) was dropwise added 1.6 M of n-butyl lithium (10 mL, 15 mmol) under $N_2$ at −78° C. while maintaining a good stirring. After stirring for 1 h, trimethyl borate (2.0 mL, 18 mmol) was added in one portion, and then the mixture was stirred for 1 h at −78° C. Water and HCl (3M) were in turn added when the mixture was naturally warmed to −30° C. Then the reaction mixture was poured into water wad extracted with ethyl acetate (3×50 mL). The combined organic phase was dried with anhydrous $Na_2SO_4$, filtered and evaporated to dryness under 35° C. The crude product was then loaded on silica gel column and eluted with dichloromethane and petroleum ether/ethyl acetate affording a pale-white solid (3.6 g, 68%). $^1$H NMR (400 MHz, DMSO-$d_6$, δ) 8.59 (s, 1H), 8.10 (d, J=7.6 Hz, 1H), 7.93-7.88 (m, 3H), 7.59-7.52 (m, 2H), 7.45-7.41 (m, 1H), 7.22-7.18 (m, 1H), 4.39-4.37 (m, 2H), 1.76-1.74 (m, 2H), 1.25-1.16 (m, 14H), 0.84 (t, J=7.4 Hz, 3H). $^{13}$C NMR (100 MHz, DMSO-$d_6$, δ)

141.6, 140.1, 131.8, 125.5, 122.3, 121.5, 119.9, 118.9, 109.3, 108.3, 42.2, 31.3, 28.9, 28.8, 28.7, 28.6, 28.5, 26.5, 22.1, 13.9. MS (FAB): m/z (M$^+$).

3,3'-Bis(N-decyl-3-carbazol)-2,2'-bithiophene (17). The synthetic procedure of 12a was followed using boronic acid R$_3$—B(OH)$_2$ (630 mg, 1.8 mmol), 11 (243 mg, 0.75 mmol), Pd(PPh$_3$)$_4$ (50 mg), THF (30 mL) and 2 M K$_2$CO$_3$ (3.6 mL). The crude product was purified by silica gel column chromatography using petroleum ether/dichloromethane as eluent affording the desired product as a colorless solid (490 mg, 84%). $^1$H NMR (400 MHz, CDCl$_3$, δ) 7.74 (d, J=8.0 Hz, 2H), 7.62 (d, J=1.2 Hz, 2H), 7.40-7.39 (m, 4H), 7.29-7.26 (m, 2H), 7.19-7.12 (m, 6H), 7.03 (d, J=8.4 Hz, 2H), 4.07 (t, J=7.2 Hz, 4H), 1.79-1.74 (m, 4H), 1.33-1.27 (m, 28H), 0.92 (t, J=8.6 Hz, 6H). $^{13}$C NMR (100 MHz, CDCl$_3$, δ) 141.7, 140.4, 139.1, 129.8, 129.5, 126.9, 126.2, 125.4, 125.3, 122.7, 122.4, 120.3, 119.9, 118.4, 108.5, 107.8, 42.7, 31.8, 29.5, 29.4, 29.3, 28.9, 27.3, 22.7, 14.1. MS (MALDI-TOF): m/z 776.1193 (M$^+$).

4,4'-Bis(N-decyl-3-carbazol)-2,2'-di(2,2':5',2"-terthiophene-5"-carboxaldehyde)-5,5'-bithiophene (19). The synthetic procedure of 14a was followed using 4,4'-bis(N-decyl-3-carbazol)-5,5'-bithiophene-2,2'-diboronic acid 18 (357 mg, 0.41 mmol), which was prepared from 17 (400 mg, 0.51 mmol), 1.6 M n-BuLi (1.2 mL, 2.0 mmol) and trimethyl borate (0.3 mL, 3 mmol) using the standard procedure, 5-indo-2,2':5',2"-terthiophene-5"-carboxaldehyde, (363 mg, 0.9 mmol), Pd(PPh$_3$)$_4$ (40 mg), THF (20 mL) and 2M K$_2$CO$_3$ (1.0 mL). The crude solid was purified by silica gel column chromatography using petroleum ether/dichloromethane as eluent affording the desired product as a red solid (402 mg, 74%). $^1$H NMR (400 MHz, CDCl$_3$, δ) 9.87 (s, 2H), 7.72 (d, J=7.6 Hz, 2H), 7.68 (d, J=4.0 Hz, 2H), 7.58 (d, J=0.9 Hz, 2H), 7.40-7.36 (m, 2H), 7.29-7.22 (m, 8H), 7.18-7.10 (m, 10H), 7.02 (d, J=8.4 Hz, 2H), 4.03 (t, J=7.2 Hz, 4H), 1.77-1.73 (m, 4H), 1.31-1.24 (m, 28H), 0.88 (t, J=6.8 Hz, 6H). $^{13}$C NMR (100 MHz, CDCl$_3$, δ) 182.4, 146.7, 142.8, 141.5, 140.4, 139.3, 138.8, 137.4, 136.9, 136.3, 135.1, 134.4, 128.4, 126.9, 126.8, 126.3, 126.1, 125.4, 125.1, 124.5, 124.0, 122.5, 120.2, 119.9, 118.5, 108.5, 107.9, 42.8, 31.8, 29.5, 29.4, 29.3, 28.9, 27.3, 22.6, 14.1. MS (MALDI-TOF): m/z 1324.3371 (M$^+$).

ADDA-3. The synthetic procedure of ADDA-1 was followed using 19 (292 mg, 0.22 mmol), malononitrile (0.40 g, 6.1 mmol), pyridine (0.8 mL) and CHCl$_3$ (20 mL). The residual solid was purified by silica gel column chromatography using petroleum ether/dichloromethane as eluent affording a black red solid which was further purified by precipitation with CHCl$_3$/CH$_3$OH, washed with methanol and dried in vacuum affording the desired product as a black solid (266 mg, 85%). $^1$H NMR (400 MHz, CDCl$_3$, δ) 7.73 (s, 2H), 7.72 (d, J=7.6 Hz, 2H), 7.61 (d, J=4.4 Hz, 2H), 7.58 (d, J=1.2 Hz, 2H), 7.41-7.34 (m, 4H), 7.25-7.22 (m, 6H), 7.18-7.12 (m, 10H), 7.02 (d, J=8.4 Hz, 2H), 4.03 (t, J=7.2 Hz, 4H), 1.76-1.73 (m, 4H), 1.30-1.23 (m, 28H), 0.88 (t, J=6.8 Hz, 6H). $^{13}$C NMR (100 MHz, CDCl$_3$, δ) 149.9, 148.9, 142.9, 140.4, 140.3, 140.2, 139.4, 137.6, 136.2, 134.8, 133.5, 133.4, 128.6, 128.2, 127.0, 126.2, 126.1, 125.7, 125.5, 124.9, 124.6, 124.3, 122.5, 122.4, 120.2, 119.9, 118.6, 114.3, 113.5, 108.6, 108.0, 75.9, 42.9, 31.9, 29.5, 29.4, 29.3, 28.9, 27.3, 22.7, 14.1. HRMS (MALDI-TOF): calcd: For C$_{84}$H$_{72}$N$_6$S$_8$: 1421.3619. Found: 1421.3643.

Table 1 below shows a summary of the physical measurements of the tricyanovinyl-based oligothiophene Compounds 1 (PhN—OF(2)OT(n)-TCN) and 2 (PhN—OFFT-TCN). For Compound 1, n=2 and 3 (PhN—OF(2)OT(2)-TCN and PhN—OF(2)OT(3)-TCN) are embodied.

TABLE 1

Summaries of physical measurement of tricyanovinyl-based oligothiophenes (Compounds 1 and 2).

| | $\lambda^{abs}_{max}$[a]/ nm | Optical gap[c]/ eV | $E^{oxd}_{1/2}$[c]/V | $E^{red}_{1/2}$ or $E^{red}_{p}$[c]/V | HOMO[c]/ eV | LUMO[c]/ eV | Energy gap[e]/ eV | $T_g/T_m$[f]/ °C. | $T_{dec}$[g]/ °C. |
|---|---|---|---|---|---|---|---|---|---|
| Compound 1 (PhN-OF(2)OT(2)-TCN) | 603/595 | 1.73 | 0.36, 0.83 | −0.93, −1.66 | 5.16 | 3.87 | 1.29 | 113/271 | 423 |
| Compound 1 (PhN-OF(2)OT(3)-TCN) | 631/631 | 1.53 | 0.36, 0.69, 0.99 | −0.92, −1.71 | 5.16 | 3.88 | 1.28 | 115/253 | 425 |
| Compound 2 (PhN-OFFT-TCN) | 625/636 | 1.55 | 0.41, 0.92 | −0.89, −1.57 | 5.21 | 3.91 | 1.30 | 70/* | 403 |

$\lambda^{abs}_{max}$: maximum absorption wavelength;

$E^{oxd}_1$: first oxidation energy wave;

$E^{red}_1$: first reduction energy wave;

HOMO: Highest Occupied Molecular Orbital;

LUMO: Lowest Unoccupied Molecular Orbital;

$T_g$: glass-transition temperature;

$T_m$: melting temperature;

$T_{dec}$: decomposition temperature.

[a]measured in CHCl$_3$.

[b]measured in thin film.

[c]estimated from the absorption edge of thin film.

[d]determined by CV method using platinum disc electrode as a working electrode, platinum wire as a counter electrode and SCE as a reference electrode with an agar salt bridge connecting to the oligomer solution and ferrocene was used as an external standard, $E_{1/2}$ (Fc/Fc$^+$) = 0.45 V vs SCE and calculated with ferrocene (4.8 eV vs vacuum).

[e]Energy gap = HOMO-LUMO.

[f]determined by differential scanning calorimeter from re-melt after cooling with a heating rate of 40° C./min under N$_2$.

[g]determined by thermal gravimetric analyzer with a heating rate of 10° C./min under N$_2$.

Figure 1:
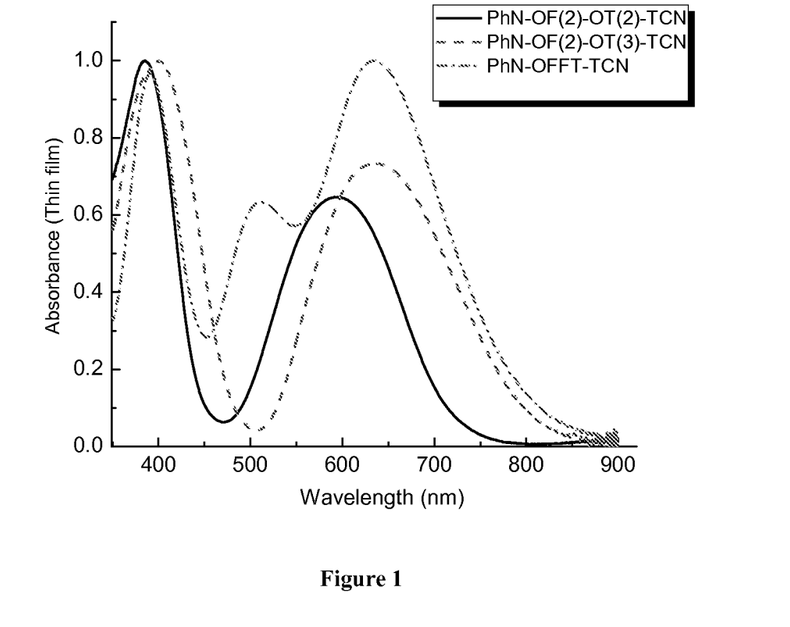
FIG. 1 shows the absorption spectra of the tricyanovinyl-based oligothiophene compounds in accordance with the present invention as measured in thin-films.

The photophysical properties of the novel tricyanovinyl-based oligothiophenes were examined by UV-vis in thin films as shown in FIG. 1. The thermal behavior and stability of these novel oligothiophenes were studied by differential scanning calorimeter (DSC) and thermal gravimetric analyses (TGA), respectively. The electrochemical properties of these oligothiophenes have been investigated by cyclic voltammetric (CV) and differential pulse voltammetric (DPV) techniques. All the results were tabulated in Table 1.

As shown in Table 1, thin films being made of the embodied tricyanovinyl-based oligothiophene compounds (Compounds 1 and 2) show an optical band-gap ranged from 1.53 eV to 1.73 eV, with Compound 1 (PhN—OF(2)OT(3)-TCN) showing the lowest optical band-gap of 1.53 eV. The strong electron-withdrawing tricyanovinyl group has efficiently lowered the lowest unoccupied molecular orbital (LUMO) level of the oligothiophenes to around 3.9 eV, which is the ideal LUMO level for matching the LUMO level of PCBM donor material for solution-processable bulk heterojunction PV cells.

Table 2 below shows a summary of the physical measurements of the dicyanovinyl-based oligothiophene Compounds 3 (ADDA-1 and ADDA-2) and 4 (ADDA-3). For Compound 3, ADDA-1 $_{n=1}$ and ADDA-2 $_{n=2}$ are embodied.

These nonplanar oligothiophenes were found to show dramatic spectral broadening and large red shifts of greater than 100 nm and up to 150 nm of absorption cutoff in solid-state thin films especially for ADDA-3 which is attributed to the restricted rotation of thiophene rings and the presence of intermolecular interactions in the solid state leading to a narrowing of optical bandgap down to 1.68 eV.

Figure 2:
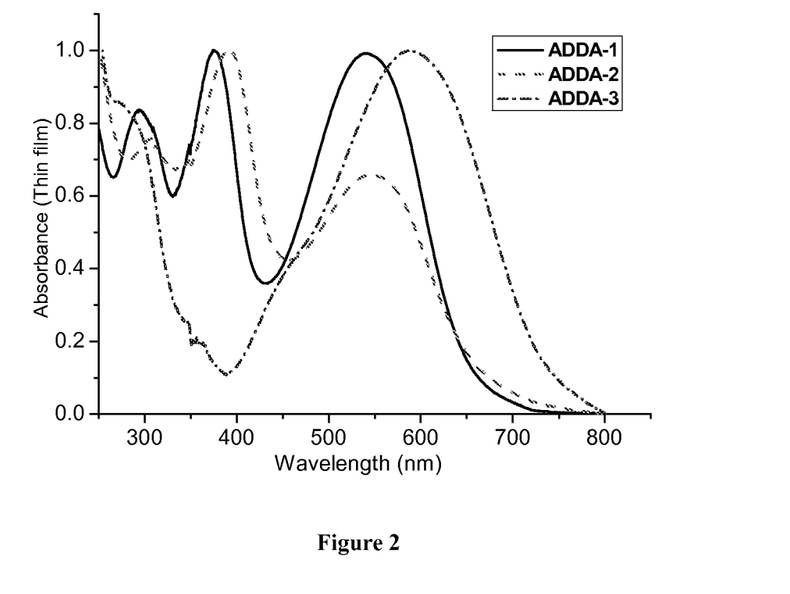
FIG. 2 shows the absorption spectra of the dicyanovinyl-based oligothiophene compounds in accordance with the present invention as measured in thin-films.

The photophysical properties of the embodied dicyanovinyl-based oligothiophene compounds (Compounds 3 and 4) were examined by UV-vis in thin films as shown in FIG. 2 and the results are tabulated in Table 2. As shown in Table 2, thin films being made of Compounds 3 and 4 show an optical band-gap ranged from 1.68 eV to 1.91 eV, with Compound 4 showing the lowest optical band-gap of 1.68 eV.

The non-planar dicyanovinyl-based oligothiophenes of Compounds 3 and 4 with two donor-acceptor systems built onto a twisted core could effectively prevent aggregation. Their physical properties in the solid state could have great improvements.

A series of novel solution-processable, p-type and low-optical-gap, double donor and double acceptor, nonplanar oligothiophenes, bearing diphenylaminofluorenyl or carbazole-derivative as a donor at 3- and 3'-positions of bithiophene core and oligothiophenes endcapped dicyanovinyl groups as acceptors have been synthesized. The three nonplanar oligothiophenes exhibit good thermal stability, strong absorption at 500-800 in thin-film and a relatively high oxidation potential at ~5.2 eV with a low optical band-gap in the range of 1.91-1.68 eV. The physical properties of these newly synthesized oligothiophenes, besides their nonplanar structure stemmed from twisted bithiophene skeleton, suggest that they are promising for solution-processable donor materials for an application of bulk heterojunction PV cells.

TABLE 2

Summaries of physical measurement of dicyanovinyl-based oligothiophenes.

| | $\lambda^{abs}_{max}{}^a$/nm | Optical gap$^c$/eV | $E^{oxd}_{1/2}{}^d$/V | $E^{red}_p{}^d$/V | HOMO$^d$/ eV | LUMO$^d$/ eV | Energy gap$^e$/eV | $T_g{}^f$/ °C. | $T_{dec}{}^g$/ °C. |
|---|---|---|---|---|---|---|---|---|---|
| ADDA-1 | 526/550$^b$ | 1.86 | 0.39, 0.60 | −1.48, −1.96 | −5.19 | −3.32 | 1.87 | 75 | 416 |
| ADDA-2 | 524/542$^b$ | 1.91 | 0.36, 0.53, 0.95 | −1.52, −1.98 | −5.16 | −3.28 | 1.88 | 150 | 416 |
| ADDA-3 | 535/593$^b$ | 1.68 | 0.37, 0.49, 0.88 | −1.47, −1.95 | −5.17 | −3.33 | 1.84 | 101 | 401 |

$\lambda^{abs}_{max}$: maximum absorption wavelength;
$E^{oxd}_1$: first oxidation energy wave;
$E^{red}_1$: first reduction energy wave;
HOMO: Highest Occupied Molecular Orbital;
LUMO: Lowest Unoccupied Molecular Orbital;
$T_g$: glass-transition temperature;
$T_m$: melting temperature;
$T_{dec}$: decomposition temperature.
$^a$measured in CHCl$_3$.
$^b$measured in thin film.
$^c$estimated from the absorption edge of thin film.
$^d$determined by CV method using platinum disc electrode as a working electrode, platinum wire as a counter electrode and SCE as a reference electrode with an agar salt bridge connecting to the oligomer solution and ferrocene was used as an external standard, $E_{1/2}$ (Fc/Fc$^+$) = 0.47 V vs SCE and calculated with ferrocene (4.8 eV vs vacuum).
$^e$Energy gap = HOMO-LUMO.
$^f$determined by differential scanning calorimeter from re-melt after cooling with a heating rate of 40° C./min under N$_2$.
$^g$determined by thermal gravimetric analyzer with a heating rate of 10° C./min under N$_2$.

The invention claimed is:
1. A compound for use in solar cell applications having a structure of Formula I:

(Formula I)

wherein n is selected from a range of 2 to 3.

2. A compound for use in solar cell applications having a structure of Formula II:

(Formula II)

3. A compound for use in solar cell applications having a structure of Formula III:

(Formula III)

wherein n is selected from a range of 1 to 2.

4. A compound for use in solar cell applications having a structure of Formula IV:

wherein n is selected from a range of 1 to 2.

* * * * *